United States Patent [19]
Potts

[11] Patent Number: 6,013,105
[45] Date of Patent: Jan. 11, 2000

[54] PROSTHESIS CONNECTOR AND ALIGNMENT ASSEMBLY

[75] Inventor: Eric P. Potts, Quilcene, Wash.

[73] Assignee: Model & Instrument Development Corporation, Poulsbo, Wash.

[21] Appl. No.: 09/038,357

[22] Filed: Mar. 10, 1998

[51] Int. Cl.⁷ ........................................................ A61F 2/62
[52] U.S. Cl. .................................................................. 623/38
[58] Field of Search .................................... 623/38, 32–37

[56] References Cited

U.S. PATENT DOCUMENTS

| 3,422,462 | 1/1969 | Finnieston | 623/38 |
| 5,443,526 | 8/1995 | Hoerner | 623/38 |

FOREIGN PATENT DOCUMENTS

| 39 37 379 A1 | 5/1991 | Germany | 623/38 |
| 2 169 207 | 7/1986 | United Kingdom | 623/38 |

OTHER PUBLICATIONS

Durr–Fillauer Orthopedic, Inc., Endoskeletal Alignment System brochure, 8 pages, Mar. 1995.

*Primary Examiner*—David H. Willse
*Attorney, Agent, or Firm*—Seed and Berry LLP

[57] ABSTRACT

An apparatus and method for positioning and/or aligning a connector between a prosthetic socket and a prosthetic limb. An alignment assembly may have a rotational positioning module and a sliding adjustment unit to position a connector at a natural joint location for a particular patient. The connector may also independently rotate with respect to the sliding adjustment unit to align the connector faces with a set of natural articulation axes of the patient. After the components are positioned and aligned, the components may be fixed together to provide a fixed connector custom fitted to a particular patient.

29 Claims, 10 Drawing Sheets

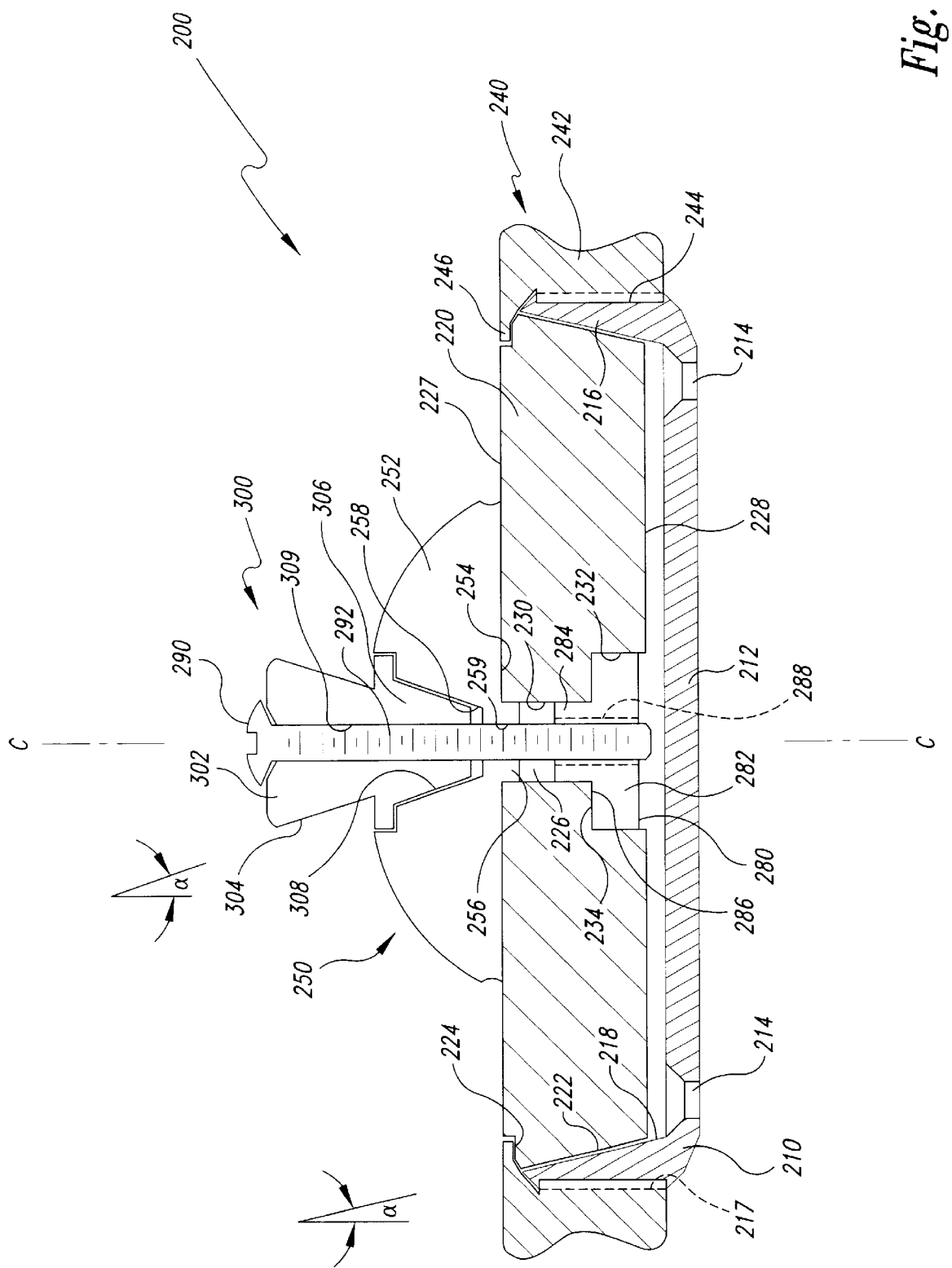

PROSTHESIS CONNECTOR AND ALIGNMENT ASSEMBLY

TECHNICAL FIELD

The present invention generally relates to a connector and an alignment assembly for positioning the connector at a desired anatomical position between a prosthetic socket and a prosthetic limb.

BACKGROUND OF THE INVENTION

Prostheses are typically lightweight components that replace damaged or missing body parts of a particular patient. Prostheses must withstand significant forces applied via complex, variable motions of the surrounding body parts. Additionally, prostheses should desirably fit and move like a natural body part of a patient. Prosthetists, therefore, often custom fit a prosthetic device to correspond to the particular anatomical features and movement of each individual patient.

Prosthetic limbs are one type of prosthesis that involve complex shapes and motions. FIG. 1A is an exploded isometric view of a conventional leg socket 10 that may be attached to a leg stump S of a particular patient P. The socket 10 typically has a lightweight liner 12 composed of a thermoplastic or fiberglass sheet. Because the leg stump S varies from one patient to another, the liner 12 is custom made to fit each patient. The leg socket 10 may also have a connector 20 with a dome 22 and an inverted pyramid 26 projecting from the dome 22. The connector 20 is generally attached to the distal end of the liner 12, and the inverted pyramid 26 is generally configured to engage a mating adapter of a lower leg prosthetic device (e.g., a pylon—not shown).

FIG. 1B is an isometric view of the leg socket 10 in which the liner 12 has a reinforced section 14 with a number of threaded holes 16. The connector 20 accordingly has an annular flange 21 with a number of elongated holes 23 to receive a plurality of bolts 18. The pyramid 26 may project from the dome 22 along the central axis C—C of the connector 20, and the pyramid 26 may have a plurality of flat faces 28 to engage the set screws of an adapter (not shown). In another prior art device shown in FIG. 1C, an off-set connector 20a has a dome 22a and a pyramid 26a positioned along an eccentric axis E—E offset from the central axis C—C of the connector 20a. To attach either of the connectors 20, 20a to the reinforced section 14, a prosthetist threads a number of bolts 18 (FIG. 1B) into the holes 16 of the reinforced section 14 (FIG. 1B).

One important aspect of attaching the connectors to the socket is to position the pyramid at a location corresponding to the natural joint for the missing limb. A prosthetist accordingly takes great care in making the liner 12 and the reinforced section 14 to position the central pyramid 26 of the connector 20 (FIG. 1B) at the natural joint location. In many applications, however, the connector 20 may not locate the central pyramid 26 at the natural joint location because the holes 16 in the reinforced section 14 are not positioned correctly or the liner 12 does not fit on the leg stump (FIG. 1A) as planned. A prosthetist may accordingly attach the off-set connector 20a (FIG. 1C) to the reinforced section 14 to position the off-set pyramid 26a at a location that best approximates the natural joint location.

One drawback of conventional systems is that it is time-consuming to attach a connector to the liner at the natural joint location. For example, the prosthetist may need to try several different off-set connectors with varying offsets to locate the pyramid at the natural joint location. The prosthetist may accordingly assemble and disassemble a prosthesis several times before finding the best connector for a particular patient. Moreover, in some cases, none of the available off-set connectors may accurately locate the off-set pyramids at the natural joint location of a particular patient. In such cases, the patients must not only learn to adapt to a prosthetic device, but they must do so with one that does not fit well or articulate in the best approximation of the natural limb. Therefore, conventional systems are time-consuming to assemble and the final prosthesis may not even fit the particular patient.

Another important aspect of attaching a connector to the reinforced section 14 is to align the faces 28 of the pyramid 26 along axes that provide the most natural articulation of the prosthetic limb. For example, natural knee joints articulate about anterior-posterior and medial-lateral axes, and the orientation of these axes varies from person to person. As such, prosthetists also try to align the pyramid faces 28 with the natural articulation axes of a specific patient. Aligning the pyramid faces 28 with the natural articulation axes of a particular patient, however, may be difficult because the position of the pyramid 26 may prevent accurate alignment of the faces 28. The prosthetist is often left with compromising between locating the pyramid at the natural joint location and aligning the pyramid faces with the natural articulation axes. Thus, conventional connectors may not provide the desired fit or articulation for a particular patient.

SUMMARY OF THE INVENTION

The present invention is an apparatus and method for positioning and/or aligning a connector between a prosthetic socket and a prosthetic limb. An alignment assembly in accordance with the invention may have a rotational positioning module and a sliding adjustment unit to position a connector at a natural joint location of a particular patient. The rotational positioning module may have a base attachable to the socket, a body moveably attached to the base, and a locking assembly coupling the body to the base. The locking assembly allows rotation between the body and the base in a released position for aligning a slot in the body with the natural joint location for the connector. The locking assembly also selectively prevents rotation between the body and the base in a locked position.

The sliding unit is attached to the rotational module. The sliding unit has a block slidably attached to the body to translate along the slot in the body, a mounting surface on the block to which a connector may be attached, and a fastening mechanism to releaseably attach the block to the body. In operation, the body is rotated to position the slot over the natural joint location, and then the slider block is moved along the slot to position the connector mounting surface at the natural joint location. A connector may then be attached to the mounting surface at the precise location of a natural joint for a particular patient.

Alternatively, the connector may be rotated independently from the block to selectively align the connector with a set of articulation axes for the particular patient. The connector is preferably attachable to the mounting surface at any alignment around a 360° circle. Thus, after the body and slider block are manipulated to position the mounting surface at the natural joint location, the connector is rotated with respect to the block to align the connector with the articulation axes. The rotational module, sliding unit and connector may then be locked together to accurately position and align the connector to fit the particular patient.

BRIEF DESCRIPTION OF THE DRAWINGS

FIG. 4 is a cross-sectional view of the alignment assembly and connector of FIGS. 2 and 3.

DETAILED DESCRIPTION OF THE INVENTION

The present invention is an apparatus and method for positioning and/or aligning a connector between a prosthetic socket and a prosthetic limb. Many specific details of certain embodiments of the invention are set forth in the following description and in FIGS. 2–9 to provide a thorough understanding of such embodiments. One skilled in the art, however, will understand that the present invention may have additional embodiments, or that the invention may be practiced without several of the details described in the following description.

Figure 1A:
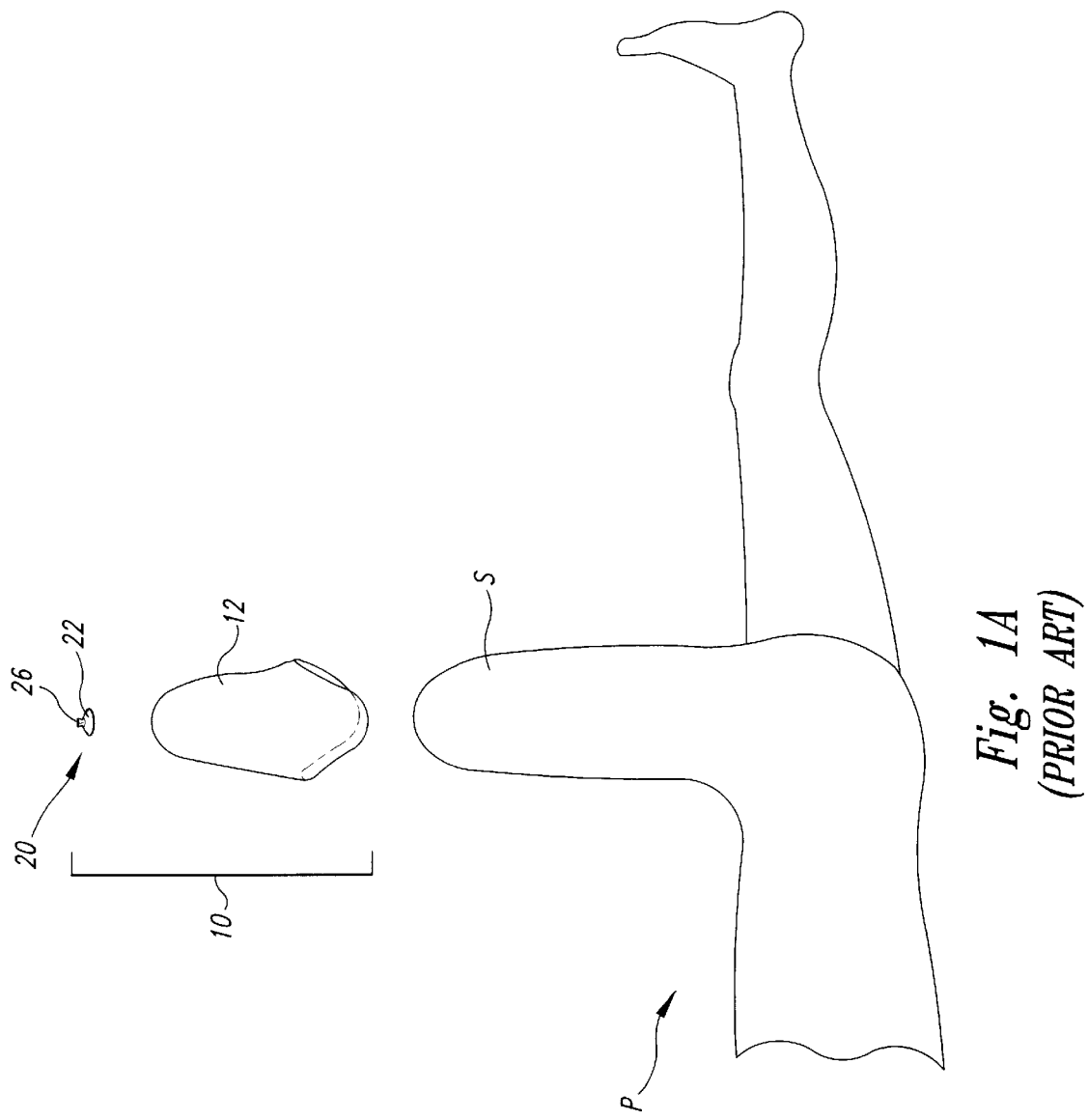
FIG. 1A is a schematic isometric view of a prosthesis with a connector in accordance with the prior art.
Figure 1B:
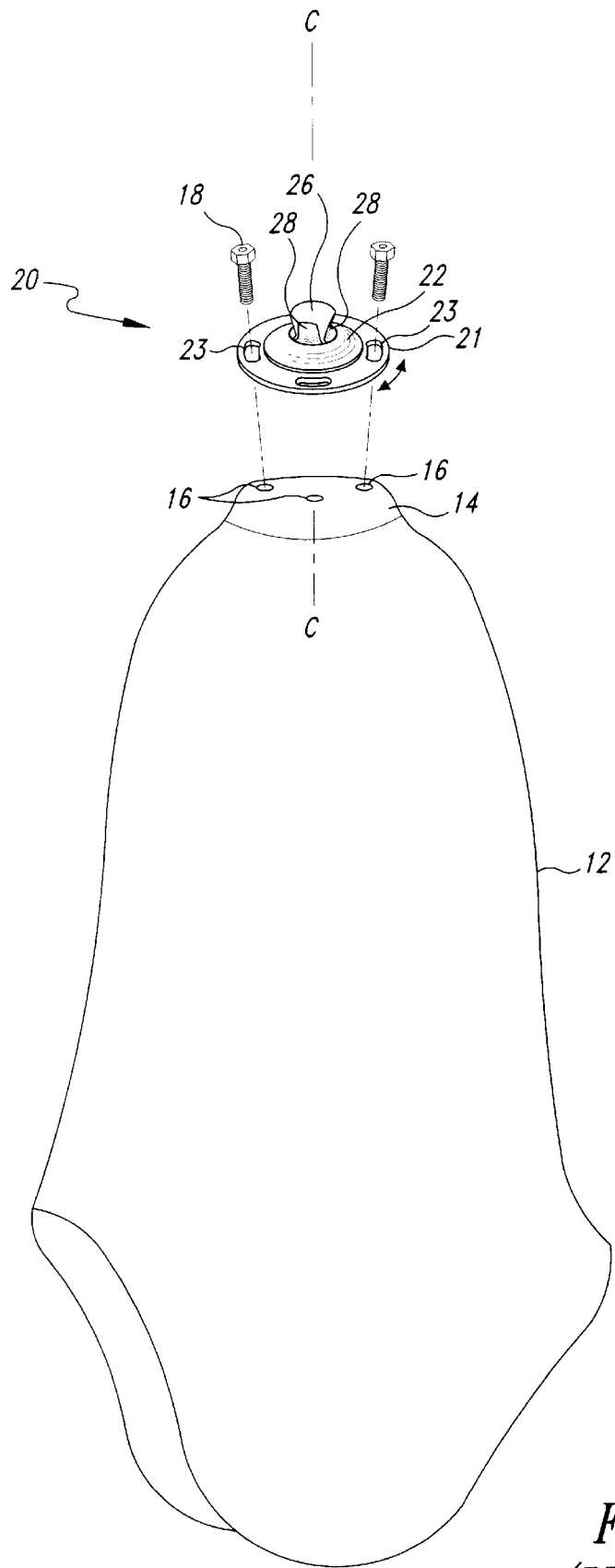
FIG. 1B is an isometric view of the prosthesis of FIG. 1A in accordance with the prior art.
Figure 1C:
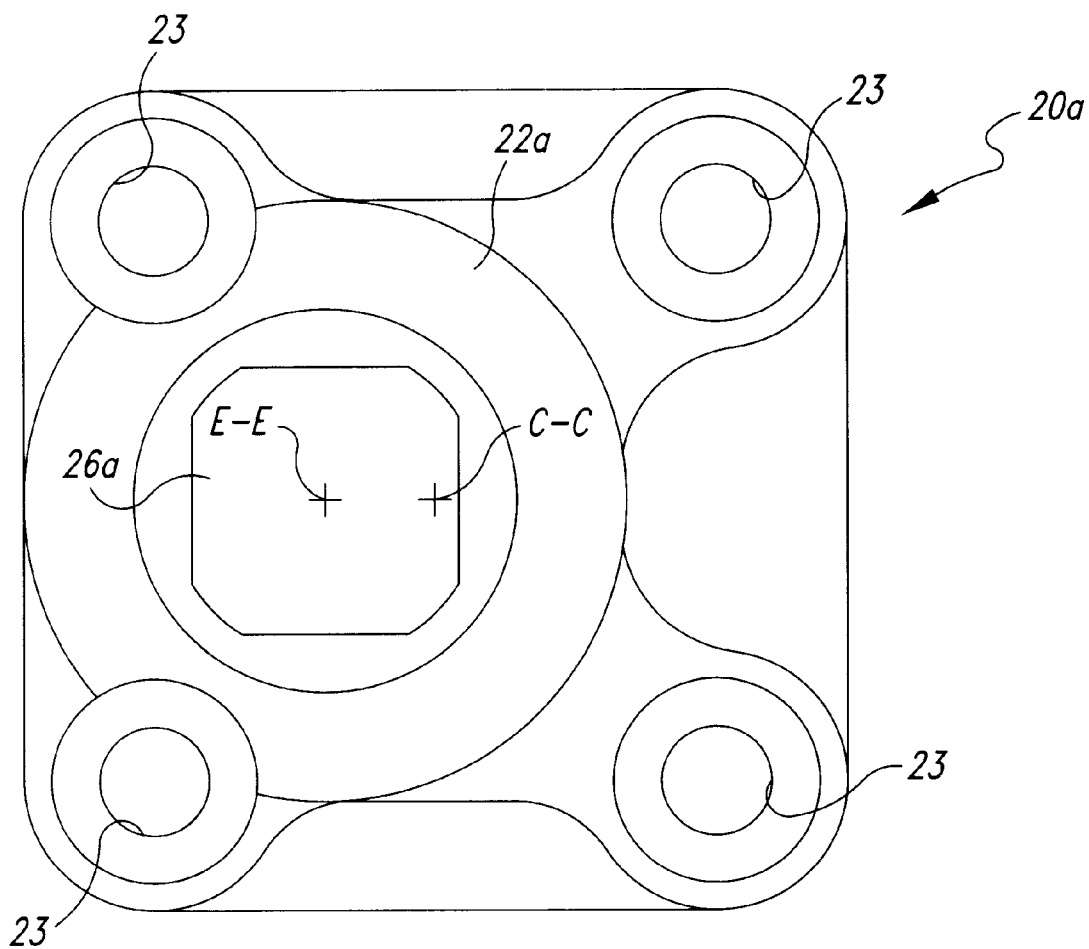
FIG. 1C is a top plan view of an off-set connector in accordance with the prior art.
Figure 2:
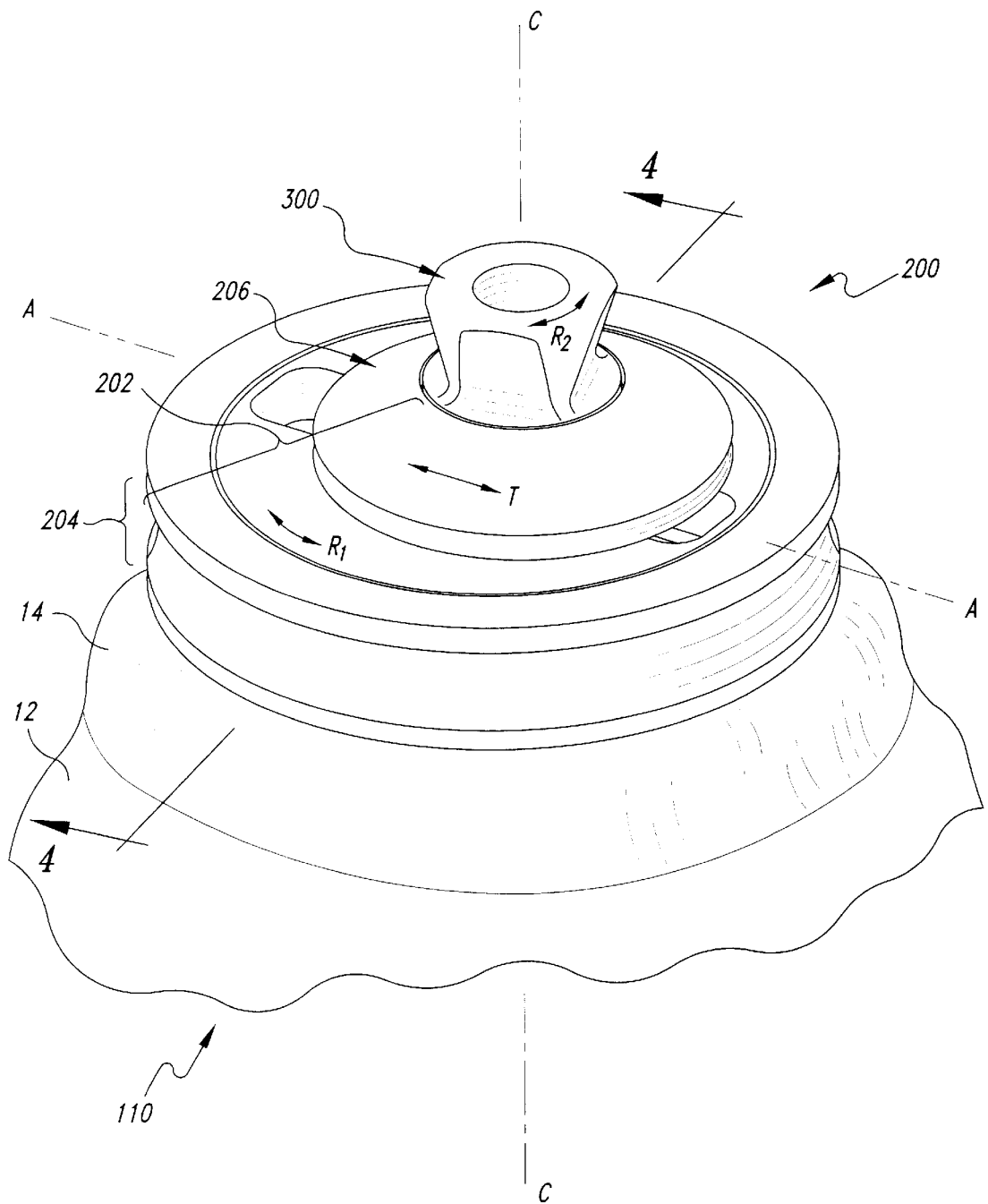
FIG. 2 is an isometric view of a prosthesis with an alignment assembly and connector in accordance with one embodiment of the invention.

FIG. 2 is an isometric view of a socket 110 with a connector assembly 200 in accordance with one embodiment of the invention. The socket 110 is a leg socket for an above-knee leg stub, but the connector assembly 200 may also be used with other sockets for below-knee leg stubs and arm stubs. In this embodiment, the general components of the connector assembly 200 include an alignment assembly 202 with a rotational positioning module 204 attached to a mounting site 14 of a liner 12, and an axial sliding unit 206 attached to the rotational module 204. The rotational module 204 may be selectively rotated with respect to the liner 12 (arrow $R_1$) to align an adjustment axis A—A of the rotational module 204 with a desired position for a connector. The sliding unit 206 is slidably attached to the rotational module 204 to be positioned along the adjustment axis A—A (arrow T). The connector assembly 200 may also include a connector 300 rotatably attached to the sliding unit 206 to rotate (arrow $R_2$) about a connector axis C—C.

In the general operation of the connector assembly 200, the rotational module 204 and the sliding unit 206 allow the connector 300 to be positioned precisely a natural joint location of a particular patient. Additionally, the connector 300 may be rotated about the connector axis C—C independently from the sliding unit 206 to align the connector 300 with a set of natural articulation axes of the particular patient. After the connector 300 is positioned and aligned to fit the particular patient, the rotational module 204, the sliding unit 206, and the connector 300 are then fixed together to prevent displacement between the components. In light of the general aspects of the connector assembly 200 described above, the specific aspects of one embodiment of a connector assembly are described below with reference to FIGS. 3–5B.

Figure 3:
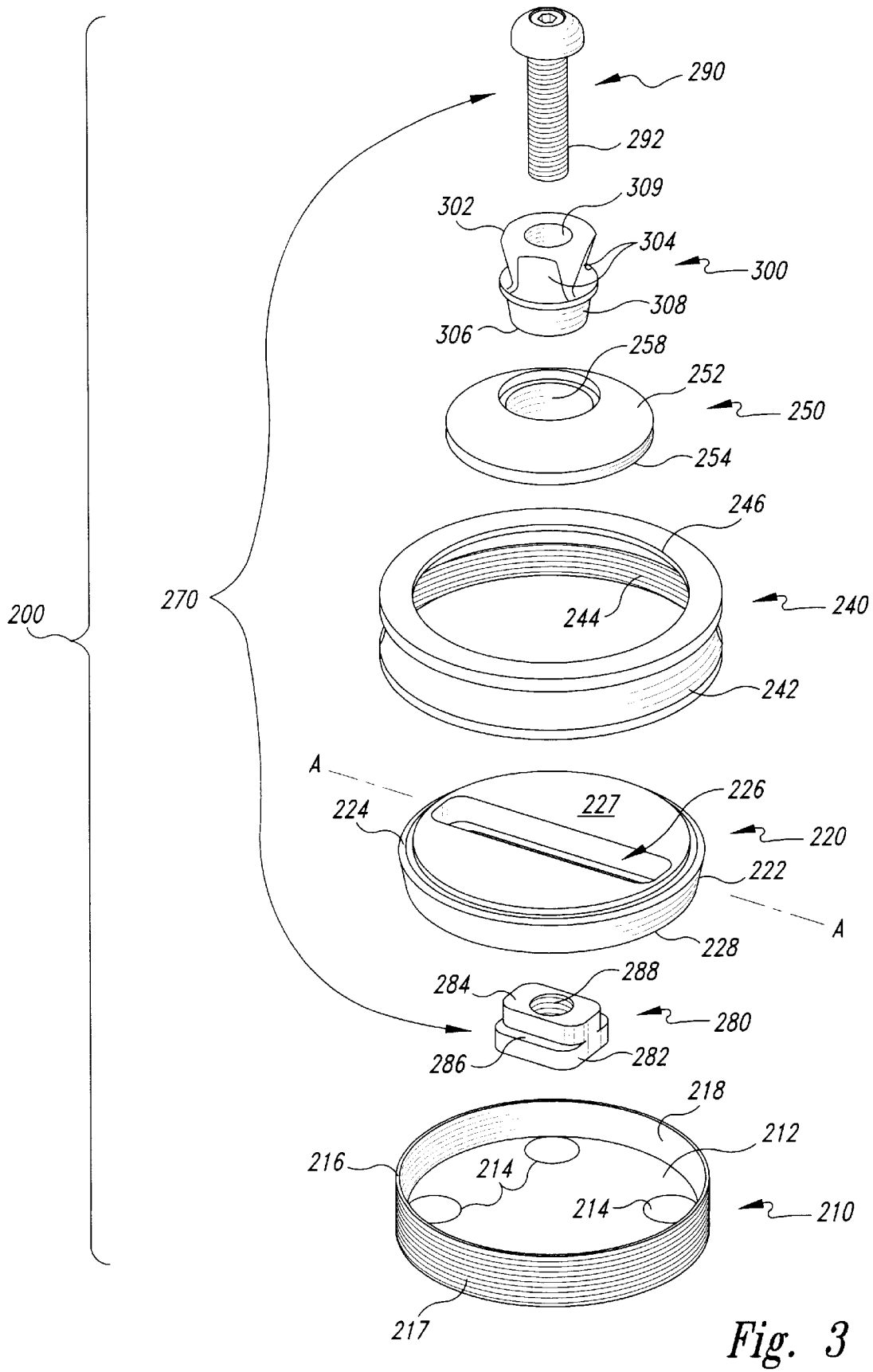
FIG. 3 is an exploded isometric view of the alignment assembly and connector of FIG. 2.

FIGS. 3 and 4 are an exploded isometric view and a cross-sectional view, respectively, of the connector assembly 200. In this embodiment, the rotational module 204 (FIG. 2) includes a base 210, a body 220 and a locking assembly 240. The base 210 may have a plate 212 with a plurality of holes 214 through which fasteners (not shown) are received to attach the base 210 to the reinforced section 14 of the liner 12 (FIG. 2). The base 210 may also have an annular wall 216 projecting from the plate 212 with a number of external threads 217 and an interior surface 218. As best shown in FIG. 4, the interior surface 218 is preferably tapered radially inwardly at an angle $\alpha$ to converge inwardly toward the plate 212.

The body 220 preferably has a circular sidewall 222 that is also preferably tapered at the angle $\alpha$ to converge inwardly toward the plate 212 of the base 210. The body 220 may also have an annular shoulder 224 extending around the top of the sidewall 222, and a slot 226 passing from a front face 227 to a back face 228. The slot 226 has a longitudinal axis that defines the adjustment axis A—A (FIG. 3) of the rotational module 204 (FIG. 2). The slot 226, more specifically, may have a front portion 230 (FIG. 4) with a first width at the front face 227, and a back portion 232 (FIG. 4) with a second width at the back face 228. In this embodiment, an interlocking surface 234 defines the boundary between the front and back portions 230 and 232 of the slot 226. The body 220 fits within the annular wall 216 of the base 210 so that the sidewall 222 of the body abuts the interior surface 218. The body 220 may accordingly rotate with respect to the base 210 for adjusting the position of the adjustment axis A—A.

The locking assembly 240 of the rotational module 204 (FIG. 2) couples the body 220 to the base 210. The locking assembly 240 may be a lock-ring 242 with a plurality of internal threads 244 that mate with the external threads 217 on the annular wall 216 projecting from the plate 212. Additionally, the locking assembly 240 may have a rim 246 projecting radially inwardly to engage the annular shoulder 224 of the body 220 (best shown in FIG. 4). When the rim 246 is disengaged from the annular shoulder 224, the locking assembly 240 allows rotation between the base 210 and the body 220 in a released position for aligning the adjustment axis A—A with a natural joint location of a particular patient. Once the adjustment axis A—A is aligned with the natural joint location, the locking-ring 242 is rotated about the base 210 to drive the rim 246 against the annular shoulder 224. As the locking-ring 242 moves toward the plate 212, the tapered sidewall 222 of the body 200 frictionally engages the tapered interior surface 218 of the base 210 to prevent the body 220 from rotating with respect to the base 210. The interior surface 218 accordingly defines a first locking element on the base 210, and the tapered sidewall 222 defines a second locking element on the body 220.

Still referring to FIGS. 3 and 4, the sliding unit 206 (FIG. 2) has a slider block 250 and a fastening mechanism 270. The slider block 250 may have a head or platform 252 with a rear surface 254 abutting the front face 227 of the body 220 (best shown in FIG. 4). The platform 252, for example, may be a dome. The slider block 250 may also have a guide portion 256 (FIG. 4) depending from the rear surface 254 to be received in the front portion 230 of the slot 226 in the body 220, a mounting surface 258 to engage the connector 300, and a bore 259 extending through the mounting surface 258 and the guide portion 256. The mounting surface 258 may be tapered inwardly at an angle α to converge toward the guide portion 256.

The fastening mechanism 270 of the sliding unit 206 may have a nut 280 received in the slot 226 of the body 220, and a fastener 290 passing through the connector 300 and the slider block 250. In this embodiment, the nut 280 is a T-nut with a first portion 282, a second portion 284 projecting from the first portion 282, and a lip 286 defined by the top surface of the first portion 282. As shown in FIG. 4, the back portion 232 of the slot 226 receives the first portion 282 of the nut 280, and the front portion 230 of the slot 226 receives the second portion 284 of the nut 280. A threaded hole 288 in the nut 280 receives a threaded shaft 292 of the fastener 290. Thus, as explained in more detail below in connection with the connector 300, the fastener 290 draws the nut 280 upward driving the lip 286 of the nut 280 against the interlocking surface 234 on the body (FIG. 4) to fixedly attach the slider block 250 to the body 220.

The connector 300 of the connector assembly 200 has a pyramid 302, a number of inclined faces 304 on the pyramid 302, and a tapered hub 306. The hub 306 is preferably tapered at the same angle α as the mounting surface 258 of the slider block 250. Additionally, the connector 300 may have a hole 309 aligned with the hole 259 in the slider block 250. The connector 300 may be fixedly attached to the slider block 250, and the slider block 250 may be fixedly attached to the body 220. For example, as the fastener 290 is tightened, it drives the tapered hub 306 against the tapered mounting surface 258, and it clamps the body 220 between the slider block 250 and the nut 280. The fastener 290 accordingly simultaneously attaches the connector 300 to the slider block 250, and the slider block 250 to the body 220.

Figure 5A:
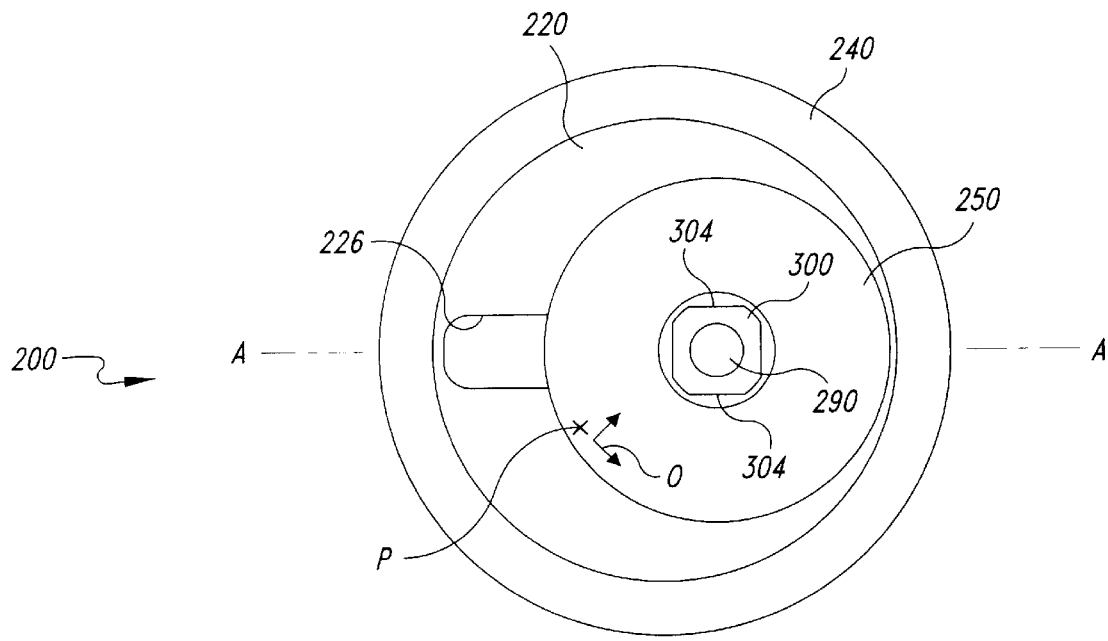
FIG. 5A is a top plan view of the alignment assembly and connector of FIG. 2 illustrating one aspect of operating the device.
Figure 5B:
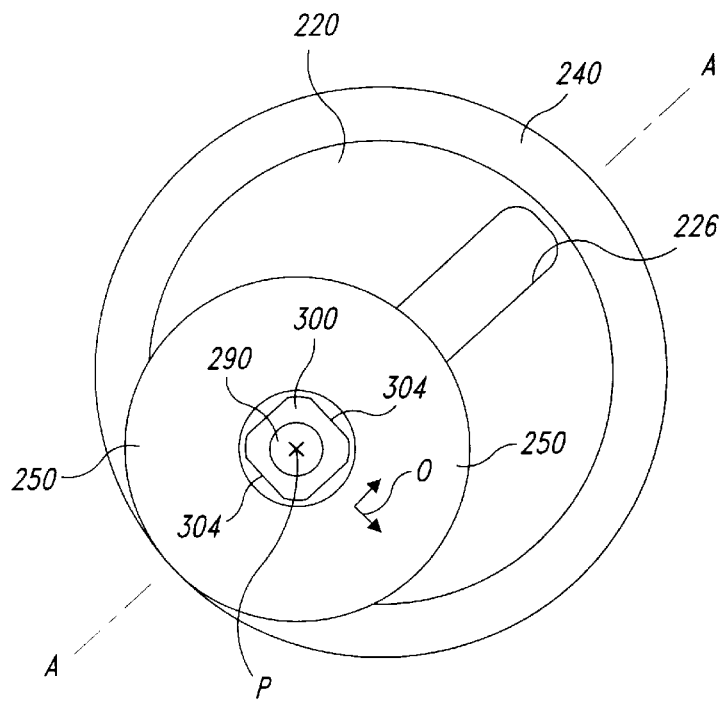
FIG. 5B is a top plan view of the alignment assembly and connector of FIG. 2 illustrating another aspect of operating the device.

FIGS. 5A and 5B are top plan views of the alignment assembly 200 illustrating the cooperative operation between the rotation module 204 (FIG. 2), the sliding unit 206 (FIG. 2), and the connector 300 to position the connector 300 at the natural joint location and align the connector faces 304 with the natural articulation axes. FIG. 5A, more specifically, illustrates the alignment assembly 200 before the connector 300 is positioned at a natural joint location P and before the connector faces 304 are aligned with a set of natural articulation axes O. To position the connector 300 at the natural joint location P, the locking assembly 240 is loosened from the body 220, and the fastener 290 is loosened from the connector 300. As shown in FIG. 5B, the body 220 is then rotated to align the adjustment axis A—A with the natural joint location P, and the slider block 250 is moved along the slot 226 until the connector 300 is positioned at the natural joint location P. To align the connector faces 304 with the natural articulation axes O, the connector 300 is then rotated with respect to the slider block 250. At this point, the locking assembly 240 is tightened to fix the body 220 to the base 210. Additionally, the fastener 290 is tightened to fix the body 220 to the slider block 250 and to fix the connector 300 to the slider block 250.

The alignment assembly 200 and the connector 300 are expected to significantly reduce the time required to accurately attach a connector to a leg socket compared to conventional connectors. Unlike conventional connectors that are often attached and then detached from a socket until the best connector for a particular patient is identified, the alignment assembly 200 may be attached to the socket and then manipulated to position and align the connector 300. Moreover, the alignment assembly 200 may be manipulated very quickly and without being removed from the socket. Thus, the alignment assembly 200 and the connector 300 are expected to provide quick, easy assembly of prosthetic limbs.

The alignment assembly 200 and the connector 300 also act together to accurately position the connector 300 at a desired natural joint location and to accurately align the connector faces 304 with a desired set of articulation axes. Because the body 220, the sliding unit 206 and the connector 300 may be positioned independently from one another, the alignment assembly 200 and the connector 300 provide universal positioning and alignment of the connector 300 without removing the base 210 from the socket. As such, the connector assembly 200 can be manipulated to connect a prosthetic limb to a socket for custom fitting a prosthetic device to a particular patient.

Figure 6:
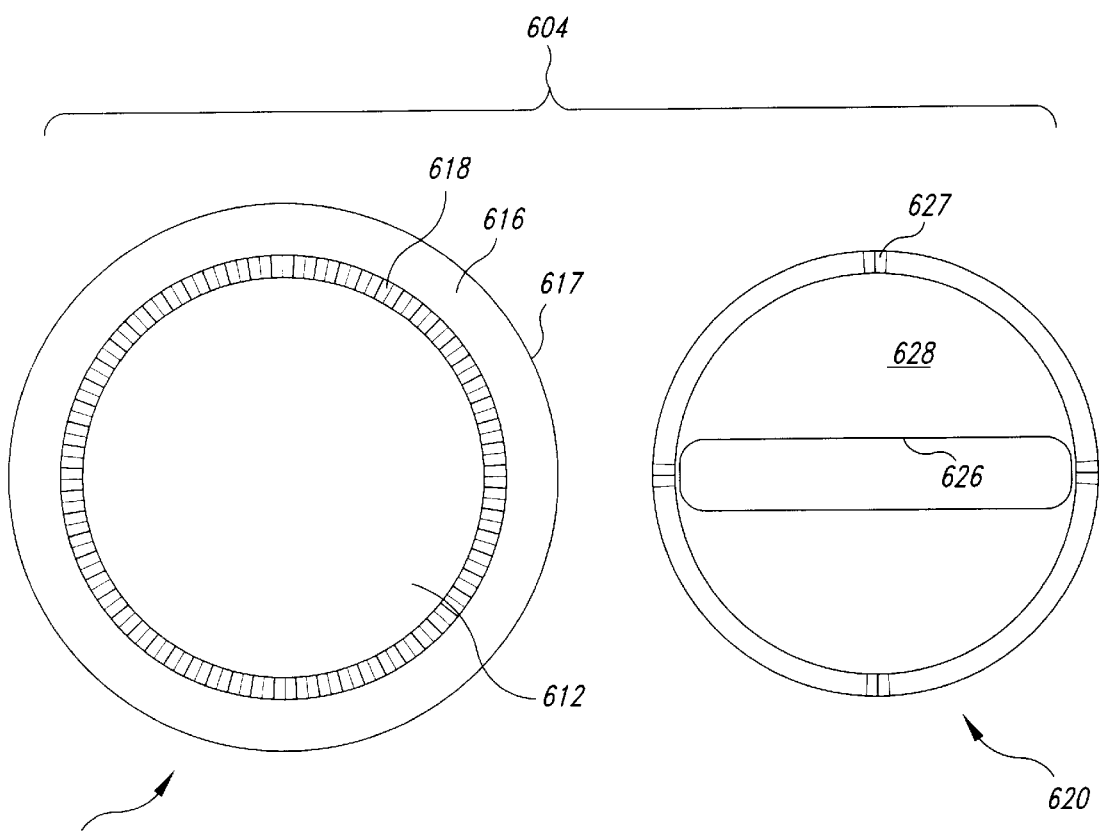
FIG. 6 is a combination view having a top plan view of a base and a bottom plan view of a body for a rotational positioning module for another alignment assembly in accordance with another embodiment of the invention.

FIG. 6 is a combination view of another rotational module 604 showing a top plan view of another base 610 and a bottom plan view of another body 620 in accordance with another embodiment of the invention. The base 610 has a plate 612, an annular wall 616 projecting from the plate 612, and a ring of teeth 618 within the wall 616. The annular wall 616 may also have a number of external threads 617 to mate with the locking-ring 242 (FIG. 2). The rotational module 604 also has a body 620 with a slot 626 and a number of teeth 627 projecting from a back surface 628 of the body. In operation, the body 620 is flipped over so that the teeth 627 of the body 620 mate with selected teeth 618 of the base 610. The locking-ring 242 (FIG. 2) may then be threaded onto the base 610 to hold the body 620 against the base 610. Accordingly, the teeth 618 on the base define another first locking element and the teeth 627 on the body define another second locking element to prevent the body 620 from rotating with respect to the base 610.

Figure 7:
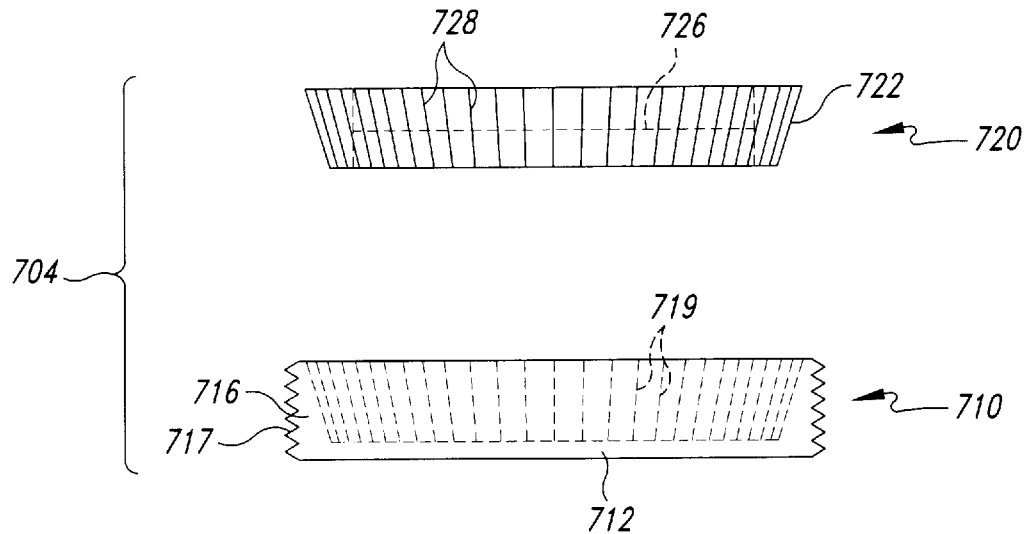
FIG. 7 is an exploded side elevational view of yet another rotational positioning module for an alignment assembly in accordance with yet another embodiment of the invention.

FIG. 7 is an exploded side elevational view of another rotational module 704 with a base 710 and a body 720 in accordance with another embodiment of the invention. The base 710 has a plate 712, a wall 716 projecting from the plate 712, a plurality of external threads 717 on the outer surface of the wall 716, and a plurality of teeth or splines 719 on the inner surface of the wall 716. The body 720 has a sidewall 722, a slot 726 (shown in phantom) extending through the body 720, and plurality of teeth or splines 728 on the sidewall 722. The splines 719 of the base 710 mesh with the splines 728 of the body 720 to prevent rotation between the base 710 and the body 720. Accordingly, the locking-ring 242 (FIG. 2) may be threaded onto the threads 717 of the base 710 to hold the body 720 against the base 710.

Figure 8:
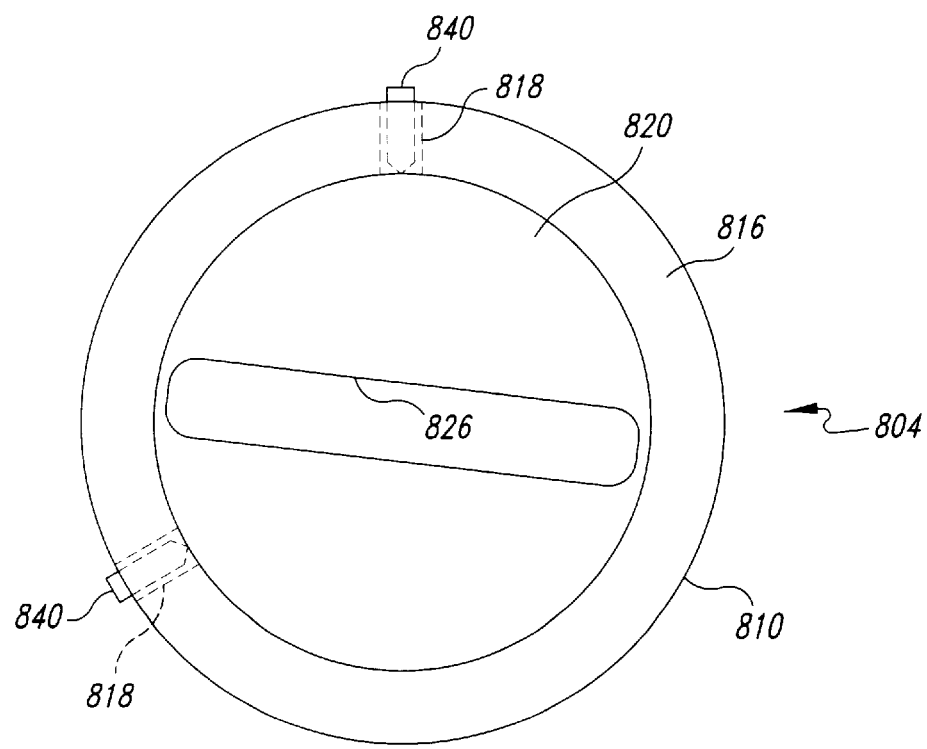
FIG. 8 is a top plan view of still another rotational positioning module for an alignment assembly in accordance with still another embodiment of the invention.

FIG. 8 is a top plan view of another rotational module 804 with a base 810 and a body 820 in accordance with still another embodiment of the invention. In this embodiment, the base 810 has a wall 816 and a plurality of holes 818 through the wall 816. The body 820 has a slot 826 similar to the body 220 described above with reference to FIGS. 2–4. The locking assembly 840 may be a number of set screws received in the threaded holes 818 of the base 810. In operation, therefore, the body 820 may be secured to the base 810 by driving the set screws 840 against the body 820.

Figure 9:
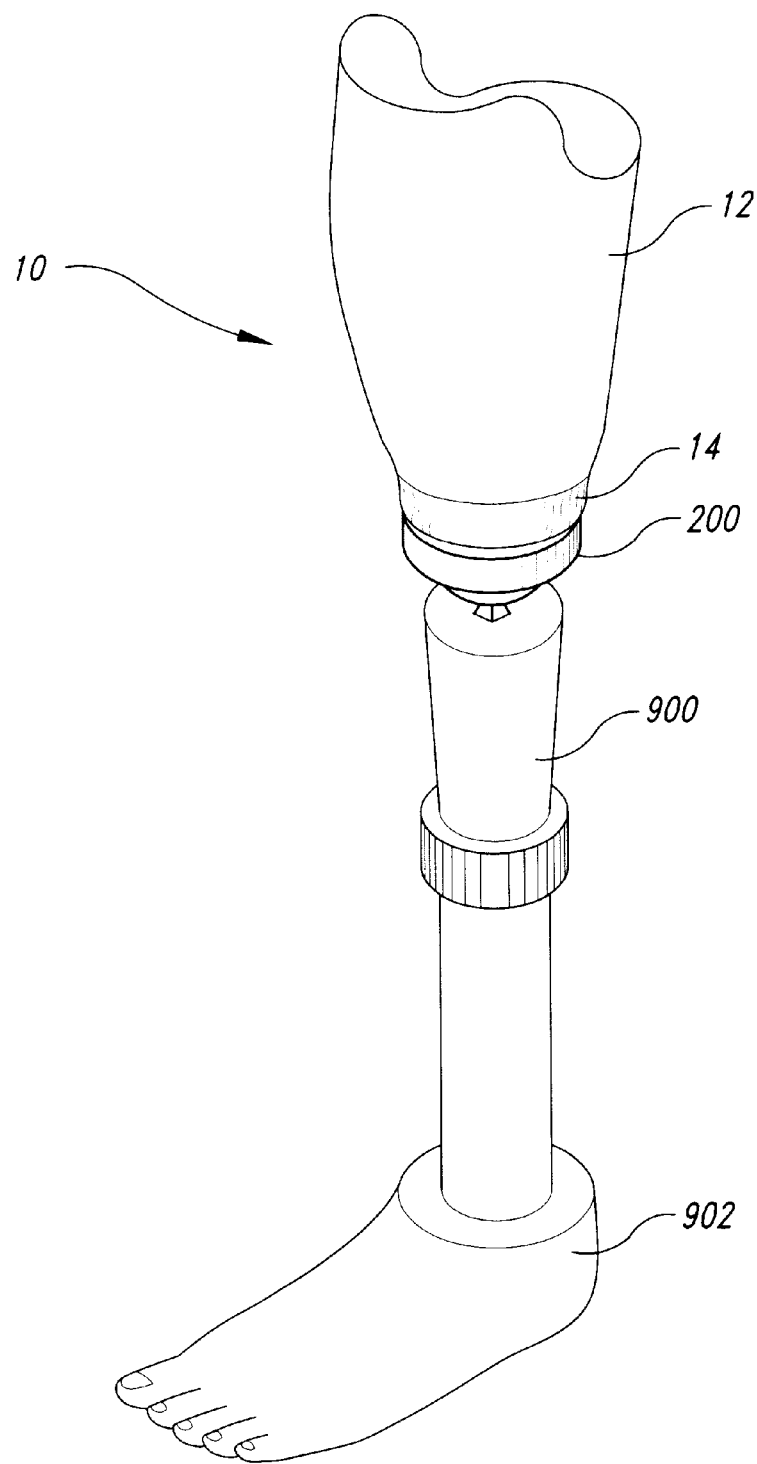
FIG. 9 is an isometric view of a lower limb prosthesis with an alignment assembly and connector in accordance with an embodiment of the invention.

FIG. 9 is an isometric view of a lower limb prosthesis in accordance with the invention having the socket 10, the alignment assembly 200 connected to the socket 10, and a lower leg pylon 900 attached to the alignment assembly 200. As set forth above, the connector 300 (FIG. 2) may be attached to the alignment assembly 200. The pylon 900 may accordingly have an adapter (not shown) that attaches to the connector 300. It will be appreciated that attaching the pylon 900 to a pyramid connector is well known in the art. A foot 902 may also be attached to the pylon 900.

From the foregoing it will be appreciated that, although specific embodiments of the invention have been described herein for purposes of illustration, various modifications may be made without deviating from the spirit and scope of the invention. For example, instead of tapered surfaces on the hub of the connector and the mounting surface of the slider block, these components may have teeth or splines similar to those shown in FIGS. 6 and 7 on the bases and bodies of the rotational positioning modules 604 and 704. Accordingly, the invention is not limited except as by the appended claims.

I claim:

1. A prosthetic limb alignment assembly for positioning a connector at a desired location between a prosthetic socket and a prosthetic limb, comprising:

a rotational positioning module having a base attachable to the socket, a body moveably attached to the base, and a locking assembly coupling the body to the base, the locking assembly allowing rotation between the body and the base in a released position for aligning an adjustment axis along the body with the desired location for the connector, and the locking assembly selectively preventing rotation between the body and the base in a locked position, wherein the base comprises a plate configured to be attached to the socket, a first locking element, and an annular wall projecting from the plate, the annular wall having an exterior surface with a plurality of external threads and an interior surface defining the first locking element, wherein the body is configured to be received within the annular wall and has an elongated slot extending along the adjustment axis and a sidewall defining a second locking element configured to engage the first locking element of the base, and wherein the locking assembly comprises a lock-ring with a plurality of internal threads to engage the external threads on the annular wall and a rim projecting inwardly to engage the body as the locking assembly is threaded onto the base, the locking assembly holding the body against the base; and an axial sliding unit attached to the rotational module, the sliding unit having a slider block slidably attached to the body to translate along the adjustment axis, a mounting surface on the slider block to which a connector may be attached, and a fastening mechanism to releasably attach the slider block to the body, the slider block being translated along the adjustment axis to position the mounting surface at the desired location.

2. The assembly of claim 1 wherein:

the first locking element comprises first splines around the interior surface of the annular wall of the base; and the second locking element comprises second splines around the sidewall of the body, the first and second splines engaging one another to prevent rotation between the body and the base.

3. The assembly of claim 1 wherein:

the interior surface is tapered radially inwardly to converge toward the plate at an angle to define the first locking element; and the sidewall is tapered radially inwardly to converge toward the plate at the angle to define the second locking element, the taper of the interior surface and the sidewall frictionally engaging the body to the base as the locking assembly threads onto the base.

4. A prosthetic limb alignment assembly for positioning a connector at a desired location between a prosthetic socket and a prosthetic limb, comprising:

a rotational positioning module having a base configured to be attached to the socket, a body moveably attached to the base including a front face, a back face, an elongated slot extending along an adjustment axis with a front portion having a first width at the front face, a back portion with a second width at the back face, and an interlocking surface between the front and back portions of the slot, and the rotational positioning module also having a locking assembly coupling the body to the base, the locking assembly allowing rotation between the body and the base in a released position for aligning the elongated slot in the body with the desired location for the connector, and the locking assembly selectively preventing rotation between the body and the base in a locked position; and an axial sliding unit attached to the rotational module, the sliding unit having a slider block slidably attached to the body to translate along the adjustment axis, the slider block including a platform with a rear surface abutting the front face of the body, a guide portion depending from the rear surface received in the front portion of the slot, a mounting surface to receive a connector, and a hole extending from the mounting surface through the guide portion, the slider block being translated along the adjustment axis to position the mounting surface at the desired location, wherein the platform comprises a dome and the mounting surface is a tapered surface angled radially inwardly to converge toward the guide portion, and the axial sliding unit further including a fastening mechanism to releasably attach the slider block to the body, and the fastening mechanism having a nut received in the slot to engage the interlocking surface and a bolt positioned through the hole in the block and threadedly engaged with the nut, the bolt drawing the block against the front face of the body and the nut against the interlocking surface to prevent movement between the body and the block.

5. A prosthetic limb alignment assembly for positioning a connector at a desired location between a prosthetic socket and a prosthetic limb, comprising:

a rotational positioning module having a base configured to be attached to the socket, a body moveably attached to the base, and a locking assembly coupling the body to the base, the locking assembly allowing rotation between the body and the base in a released position for aligning an adjustment axis along the body with the desired location for the connector, and the locking assembly selectively preventing rotation between the body and the base in a locked position, wherein the base comprises a plate configured to be attached to the socket and an annular wall projecting from the plate, the annular wall having an exterior surface with a plurality of external threads and an interior surface defining a first locking element, wherein the body is configured to be received within the annular wall and has a front face, a back face, an elongated slot extending along the adjustment axis with a front portion having a first width at the front face, a back portion with a second width at the back face, and an interlocking surface between the front and back portions of the slot, and a sidewall defining a second locking element to engage the first locking element, and wherein the locking assembly comprises a lock-ring with a plurality of internal threads to engage the external threads on the annular wall and a rim projecting inwardly to engage the body as the locking assembly is threaded onto the base, the locking assembly holding the body against the base; and an axial sliding unit attached to the rotational module, the sliding unit having a slider block slidably attached to the body to translate along the adjustment axis, the slider block including a platform with a rear surface abutting the front face of the body, a guide portion depending from the rear surface received in the front portion of the slot, a mounting surface to receive a connector, and a hole extending from the mounting surface through the guide portion, the slider block being translated along the adjustment axis to position the mounting surface at the desired location, and the axial sliding unit further including a fastening mechanism to releasably attach the slider block to the body, the fastening mechanism having a nut received in the slot to engage the interlocking surface and a bolt positioned through the hole in the block and threadedly engaged with the nut, the bolt drawing the block against the front face of the body and the nut against the interlocking surface to prevent movement between the body and the block.

6. The assembly of claim 5 wherein:

the first locking element comprises first splines around the interior surface of the annular wall; and the second locking element comprises second splines around the sidewall, the first and second splines engaging one another to prevent rotation between the body and the base.

7. The assembly of claim 5 wherein:

the interior surface is tapered radially inwardly to converge toward the plate at an angle to define the first locking element; and the sidewall is tapered radially inwardly to converge toward the plate at the angle to define the second locking element, the taper of the interior surface and the sidewall frictionally engaging the body to the base as the locking assembly threads onto the base.

8. A prosthetic limb alignment assembly for positioning a connector between a prosthetic socket and a prosthetic limb, comprising:

a base attachable to the socket, the base having a plate, a first locking element, and an annular wall projecting from the plate, the annular wall having an exterior surface with a plurality of external threads and an interior surface defining the first locking element;

a body configured to be received within the annular wall is rotatably attached to the base, the body having an elongated slot extending along an adjustment axis, a second locking element configured to releasably engage the first locking element of the base, and a sidewall defining the second locking element;

a releasable locking assembly coupled to the base and the body, the locking assembly holding the first locking element against the second locking element to prevent rotation between the base and the body in a locked position and the locking assembly releasing the first and second locking elements from one another to allow rotation between the base and the body in an adjustment position, wherein the locking assembly comprises a lock-ring with a plurality of internal threads to engage the external threads on the annular wall and a rim projecting inwardly to engage the body as the locking assembly is threaded onto the base, the locking assembly holding the body against the base;

a block having a guide member configured to slide in the slot and a head with a mounting surface to which a connector may be attached; and a fastening mechanism to releasably attach the block to the body along the adjustment axis.

9. The assembly of claim 8 wherein:

the first locking element comprises first splines around the interior surface of the annular wall of the base; and the second locking element comprises second splines around the sidewall of the body, the first and second splines engaging one another to prevent rotation between the body and the base.

10. The assembly of claim 8 wherein:

the interior surface is tapered radially inwardly to converge toward the plate at an angle to define the first locking element; and the sidewall is tapered radially inwardly to converge toward the plate at the angle to define the second locking element, the taper of the interior surface and the sidewall frictionally engaging the body to the base as the locking assembly threads onto the base.

11. A prosthetic limb alignment assembly for positioning a connector between a prosthetic socket and a prosthetic limb, comprising:

a base attachable to the socket, the base having a plate configured to be attached to the socket and a first locking element;

a body rotatably attached to the base, the body having a front face, a back face, an elongated slot extending along an adjustment axis having a front portion with a first width at the front face, a back portion with a second width at the back face, and an interlocking surface between the front and back portions of the slot, and the body also having a second locking element configured to releasably engage the first locking element of the base;

a releasable locking assembly coupled to the base and the body, the locking assembly holding the first locking element against the second locking element to prevent rotation between the base and the body in a locked position and the locking assembly releasing the first and second locking elements from one another to allow rotation between the base and the body in an adjustment position;

a block having a guide member configured to slide in the slot and a head with a mounting surface to which a connector may be attached, wherein the head of the block has a rear surface abutting the front face of the body, a guide portion depending from the rear surface received in the front portion of the slot, and a hole extending through the block, and wherein the head comprises a dome and the mounting surface is a tapered surface angled radially inwardly to converge toward the guide portion; and a fastening mechanism to releasably attach the block to the body along the adjustment axis, the fastening mechanism comprising a nut received in the slot to engage the interlocking surface and a bolt positioned through the hole in the block and threadedly engaged with the nut, the bolt drawing the block against the front face of the body and the nut against the interlocking surface to prevent movement between the body and the block.

12. A prosthetic limb alignment assembly for positioning a connector between a prosthetic socket and a prosthetic limb, comprising:

a base attachable to the socket, the base having a plate configured to be attached to the socket, a first locking element, and an annular wall projecting from the plate, the annular wall having an exterior surface with a plurality of external threads and an interior surface defining the first locking element;

a body configured to be received within the annular wall is rotatably attached to the base, the body having a front face, a back face, an elongated slot extending along an adjustment axis having a front portion with a first width at the front face, back portion with a second width at the back face, and an interlocking surface between the front and back portions of the slot, and the body also including a sidewall defining a second locking element configured to releasably engage the first locking element of the base;

a releasable locking assembly coupled to the base and the body, the locking assembly holding the first locking element against the second locking element to prevent rotation between the base and the body in a locked position and the locking assembly releasing the first and second locking elements from one another to allow rotation between the base and the body in an adjustment position, wherein the locking assembly comprises a lock-ring with a plurality of internal threads to engage the external threads on the annular wall and a rim projecting inwardly to engage the body as the locking assembly is threaded onto the base, the locking assembly holding the body against the base;

a block having a guide member configured to slide in the slot and a head with a mounting surface to which a connector may be attached, wherein the head of the block has a rear surface abutting the front face of the body, a guide portion depending from the rear surface received in the front portion of the slot, and a hole extending through the block; and a fastening mechanism to releasably attach the block to the body along the adjustment axis, the fastening mechanism comprising a nut received in the slot to engage the interlocking surface and a bolt positioned through the hole in the block and threadedly engaged with the nut, the bolt drawing the block against the front face of the body and the nut against the interlocking surface to prevent movement between the body and the block.

13. The assembly of claim 12 wherein:

the first locking element comprises first splines around the interior surface of the annular wall of the base; and the second locking element comprises second splines around the sidewall of the body, the first and second splines engaging one another to prevent rotation between the body and the base.

14. The assembly of claim 12 wherein:

the interior surface is tapered radially inwardly to converge toward the plate at an angle to define the first locking element; and the sidewall is tapered radially inwardly to converge toward the plate at the angle to define the second locking element, the taper of the interior surface and the sidewall frictionally engaging the body to the base as the locking assembly threads onto the base.

15. A connector assembly for attaching a prosthetic socket to a prosthetic limb, comprising:

a rotational positioning module having a base attachable to the socket, a body moveably attached to the base, and a locking assembly coupling the body to the base, the locking assembly allowing rotation between the body and the base in a released position for aligning an adjustment axis along the body with a desired connector location, and the locking assembly selectively preventing rotation between the body and the base in a locked position, the base comprising a plate configured to be attached to the socket and a first locking element, and the body comprising an elongated slot extending along the adjustment axis and a second locking element configured to engage the first locking element of the base, wherein the base further comprises an annular wall projecting from the plate, the annular wall having an exterior surface with a plurality of external threads and an interior surface defining the first locking element, wherein the body is configured to be received within the annular wall and has a sidewall defining the second locking element to engage the first locking element, and wherein the locking assembly comprises a lock-ring with a plurality of internal threads to engage the external threads on the annular wall and a rim projecting inwardly to engage the body as the locking assembly is threaded onto the base, the locking assembly holding the body against the base;

an axial sliding unit attached to the rotational positioning module, the sliding unit having a slider block slidably attached to the body to translate along the adjustment axis, a mounting surface on the slider block, and a fastening mechanism to releasably attach the slider block to the body, the slider block being translated along the adjustment axis to position the mounting surface at the desired location; and a connector attached to the mounting surface, the connector configured to engage an end of the prosthetic limb to define a joint between the prosthetic limb and the prosthetic socket.

16. The assembly of claim 15 wherein:

the first locking element comprises first splines around the interior surface of the annular wall of the base; and the second locking element comprises second splines around the sidewall of the body, the first and second splines engaging one another to prevent rotation between the body and the base.

17. The assembly of claim 15 wherein:

the interior surface is tapered radially inwardly to converge toward the plate at an angle to define the first locking element; and the sidewall is tapered radially inwardly to converge toward the plate at the angle to define the second locking element, the taper of the interior surface and the sidewall frictionally engaging the body to the base as the locking assembly threads onto the base.

18. A connector assembly for attaching a prosthetic socket to a prosthetic limb, comprising:

a rotational positioning module having a base attachable to the socket, a body moveably attached to the base, and a locking assembly coupling the body to the base, the locking assembly allowing rotation between the body and the base in a released position for aligning an adjustment axis along the body with a desired connector location, and the locking assembly selectively preventing rotation between the body and the base in a locked position, the base comprising a plate configured to be attached to the socket and a first locking element, and the body comprising a front face, a back face, a second locking element configured to engage the first locking element of the base, and an elongated slot extending along the adjustment axis with a front portion having a first width at the front face, a back portion with a second width at the back face, and an interlocking surface between the front and back portions of the slot, wherein the base further comprises an annular wall projecting from the plate, the annular wall having an exterior surface with a plurality of external threads and an interior surface defining a first locking element, wherein the body is configured to be received within the annular wall and has a sidewall defining a second locking element to engage the first locking element, and wherein the locking assembly comprises a lock-ring with a plurality of internal threads to engage the external threads on the annular wall and a rim projecting inwardly to engage the body as the locking assembly is threaded onto the base, the locking assembly holding the body against the base;

an axial sliding unit attached to the rotational positioning module, the sliding unit having a slider block slidably attached to the body to translate along the adjustment axis, the slider block including a platform with a rear surface abutting the front face of the body, a guide portion depending from the rear surface received in the front portion of the slot, a hole extending through the block, and a mounting surface to receive a connector, the slider block being translated along the adjustment axis to position the mounting surface at the desired location, and the axial sliding unit also including a fastening mechanism to releasably attach the slider block to the body, the fastening mechanism having a nut received in the slot to engage the interlocking surface and a bolt positioned through the hole in the block and threadedly engaged with the nut, the bolt drawing the block against the front face of the body and the nut against the interlocking surface to prevent movement between the body and the block; and a connector attached to the mounting surface, the connector configured to engage an end of the prosthetic limb to define a joint between the prosthetic limb and the prosthetic socket.

19. The assembly of claim 18 wherein:

the first locking element comprises first splines around the interior surface of the annular wall; and the second locking element comprises second splines around the sidewall, the first and second splines engaging one another to prevent rotation between the body and the base.

20. The assembly of claim 18 wherein:

the interior surface is tapered radially inwardly to converge toward the plate at an angle to define the first locking element; and the sidewall is tapered radially inwardly to converge toward the plate at the angle to define the second locking element, the taper of the interior surface and the sidewall frictionally engaging the body to the base as the locking assembly threads onto the base.

21. A prosthetic limb assembly, comprising:

a socket;

a rotational positioning module having a base including a plate configured to be attached to the socket and a first locking element, a body moveably attached to the base including an elongated slot extending along an adjustment axis and a second locking element configured to engage the first locking element of the base, and a locking assembly coupling the body to the base, the locking assembly allowing rotation between the body and the base in a released position for aligning the elongated slot in the body with a desired connector location, and the locking assembly selectively preventing rotation between the body and the base in a locked position, wherein the base further comprises an annular wall projecting from the plate, the annular wall having an exterior surface with a plurality of external threads and an interior surface defining the first locking element, wherein the body is configured to be received within the annular wall and has a sidewall defining the second locking element to engage the first locking element, and wherein the locking assembly comprises a lock-ring with a plurality of internal threads to engage the external threads on the annular wall and a rim projecting inwardly to engage the body as the locking assembly is threaded onto the base, the locking assembly holding the body against the base;

an axial sliding unit attached to the rotational module, the sliding unit having a slider block slidably attached to the body to translate along the adjustment axis, a mounting surface on the slider block to which a connector may be attached, and a fastening mechanism to releasably attach the slider block to the body, the slider block being translated along the adjustment axis to position the mounting surface at the desired connector location;

a connector attached to the mounting surface; and a prosthetic limb attached to the connector.

22. The assembly of claim 21 wherein:

the first locking element comprises first splines around the interior surface of the annular wall of the base; and the second locking element comprises second splines around the sidewall of the body, the first and second splines engaging one another to prevent rotation between the body and the base.

23. The assembly of claim 21 wherein:

the interior surface is tapered radially inwardly to converge toward the plate at an angle to define the first locking element; and the sidewall is tapered radially inwardly to converge toward the plate at the angle to define the second locking element, the taper of the interior surface and the sidewall frictionally engaging the body to the base as the locking assembly threads onto the base.

24. A prosthetic limb assembly, comprising:

a socket;

a rotational positioning module having a base including a plate configured to be attached to the socket, a body moveably attached to the base including a front face, a back face, an elongated slot extending along an adjustment axis with a front portion having a first width at the front face, a back portion with a second width at the back face, and an interlocking surface between the front and back portions of the slot, and the rotational positioning module further including a locking assembly coupling the body to the base, the locking assembly allowing rotation between the body and the base in a released position for aligning the elongated slot in the body with a desired connector location, and the locking assembly selectively preventing rotation between the body and the base in a locked position, wherein the base further comprises an annular wall projecting from the plate, the annular wall having an exterior surface with a plurality of external threads and an interior surface defining a first locking element, wherein the body is configured to be received within the annular wall and has a sidewall defining a second locking element to engage the first locking element, and wherein the locking assembly comprises a lock-ring with a plurality of internal threads to engage the external threads on the annular wall and a rim projecting inwardly to engage the body as the locking assembly is threaded onto the base, the locking assembly holding the body against the base;

an axial sliding unit attached to the rotational module, the sliding unit having a slider block slidably attached to the body to translate along the adjustment axis, a mounting surface on the slider block to which a connector may be attached, and a fastening mechanism to releasably attach the slider block to the body the slider block being translated along the adjustment axis to position the mounting surface at the desired connector location, wherein the block of the sliding unit has a platform with a rear surface abutting the front face of the body, a guide portion depending from the rear surface received in the front portion of the slot, and a hole extending through the block, the mounting surface being on the platform, and the fastening mechanism comprises a nut received in the slot to engage the interlocking surface and a bolt positioned through the hole in the block and threadedly engaged with the nut, the bolt drawing the block against the front face of the body and the nut against the interlocking surface to prevent movement between the body and the block;

a connector attached to the mounting surface; and a prosthetic limb attached to the connector.

25. The assembly of claim 24 wherein:

the first locking element comprises first splines around the interior surface of the annular wall of the base; and the second locking element comprises second splines around the sidewall of the body, the first and second splines engaging one another to prevent rotation between the body and the base.

26. The assembly of claim 24 wherein:

the interior surface is tapered radially inwardly to converge toward the plate at an angle to define the first locking element; and the sidewall is tapered radially inwardly to converge toward the plate at the angle to define the second locking element, the taper of the interior surface and the sidewall frictionally engaging the body to the base as the locking assembly threads onto the base.

27. A method for positioning a prosthetic connector at a desired location with respect to a socket, comprising:

positioning an adjustment axis of a rotatable body in alignment with the desired connector location by rotating the body with respect to the socket;

moving a block attached to the body along the adjustment axis to position a mounting surface on the block at the desired location; and preventing rotation of the body and preventing translation of the block along the body after the mounting surface is positioned at the desired location, the connector being attachable to the mounting surface to be positioned at the desired location, wherein preventing rotation of the body comprises locking the body to a base attached to the socket by driving a lock-ring against the body to drive a tapered sidewall of the body against a tapered interior surface of a wall projecting from the base so that friction between the sidewall and the interior surface prevents the body from rotating with respect to the base.

28. A method for positioning a prosthetic connector at a desired location with respect to a socket, comprising:

positioning an adjustment axis of a rotatable body in alignment with the desired connector location by rotating the body with respect to a base attached to the socket;

moving a block attached to the body along the adjustment axis to position a mounting surface on the block at the desired location by sliding the block along a slot in the body extending along the adjustment axis;

preventing rotation of the body and preventing translation of the block along the body after the mounting surface is positioned at the desired location, the connector being attachable to the mounting surface to be positioned at the desired location, wherein preventing rotation of the body comprises driving a lock-ring against the body to drive a tapered sidewall of the body against a tapered interior surface of a wall projecting from the base so that friction between the sidewall and the interior surface prevents the body from rotating with respect to the base, and preventing translation of the block along the body also comprises preventing rotation of the connector with respect to the mounting surface by fastening the connector, the block and the body together; and rotating the connector with respect to the mounting surface of the block to align faces on the connector with a set of articulation axes of a patient.

29. The method of claim 28 wherein:

the mounting surface is tapered and the connector has a tapered hub received in the mounting surface; and fastening the connector, the block and the body together comprises drawing a nut threadedly attached to a bolt toward a head of the bolt so that a rear surface of the block engages the body and the tapered surface of the hub drives against the tapered mounting surface, the friction between the block and the body preventing the body from translating along the adjustment axis, and the friction between the mounting surface and the hub of the connector preventing the connector from rotating with respect to the block.

* * * * *